(12) United States Patent
Olsen et al.

(10) Patent No.: US 6,572,583 B1
(45) Date of Patent: Jun. 3, 2003

(54) BULKHEAD FOR IMPLANTABLE INFUSION DEVICE

(75) Inventors: James Olsen, Plymouth, MN (US); Steve Christenson, Coon Rapids, MN (US); Michael Hegland, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,557

(22) Filed: Apr. 28, 2000

(51) Int. Cl.$^7$ ............................................. A61M 37/00
(52) U.S. Cl. .................. 604/93.01; 604/131; 604/890.1
(58) Field of Search .............................. 604/131, 890.1, 604/93.01

(56) References Cited

U.S. PATENT DOCUMENTS

| | | | |
|---|---|---|---|
| 4,692,147 A | | 9/1987 | Duggan |
| 4,715,852 A | * | 12/1987 | Reinicke et al. ..... 128/DIG. 12 |
| 5,725,017 A | | 3/1998 | Elsberry et al. |
| 5,993,414 A | | 11/1999 | Haller |

OTHER PUBLICATIONS

"About Advanced Pain Therapies", Medtronic Synchromed Infusion System Product Information, excerpt from website, medtronic.com.

"Hepatic Arterial Infusion",Medtronic IsoMed Infusion System Product Information, excerpt from website, medtronic.com.

"Hepatic Arterial Infusion",Medtronic IsoMed Fact Sheet, excerpt from website, medtronic.com.

* cited by examiner

Primary Examiner—Edward K. Look
Assistant Examiner—Dwayne J. White
(74) Attorney, Agent, or Firm—Banner & Witcoff, Ltd.

(57) ABSTRACT

The present invention relates to an implantable medical device that is used to deliver drugs or other therapeutic agents into a patient. More specifically, the present invention is for a drug infusion device which features a bulkhead having integrated subsystems. The bulkhead is the main structural component of the implantable medical device. The integrated bulkhead of the present invention has all or portions of subassemblies, such as a pump, motor and gear train, electronics, drug fill port, catheter access port, fluid pathways, filter and overpressure mechanism, built into the bulkhead. Integrating the subsystems of the bulkhead simplifies the assembly process and reduces the overall cost of manufacture by reducing the number of components to assemble and reducing the number of manufacturing steps. Additionally, integrating the subassemblies into the bulkhead allows for increased accuracy in controlling the connections between the subsystems, which allows for improved delivery of drugs to the patient. The invention also provides a new configuration of the motor and gear train and pump sub-assemblies within the bulkhead, which provides for an implantable drug infusion pump having a low profile.

5 Claims, 6 Drawing Sheets

BULKHEAD FOR IMPLANTABLE INFUSION DEVICE

BACKGROUND OF THE INVENTION

1. Field of the Invention

The present invention relates to implantable drug delivery devices for infusing a therapeutic agent into an organism, and more particularly, relates to an improved bulkhead, which is the main structural component of an implantable drug delivery device, having integrated subsystems. The invention additionally contemplates a related method of manufacturing implantable drug delivery devices, which simplifies manufacturing and assembly processes thereby reducing the overall cost of production.

2. Description of the Related Art

Implantable drug infusion devices are well known in the art. These devices typically include a medication reservoir within a generally cylindrical housing. Some form of fluid flow control is also provided to control or regulate the flow of fluid medication from the reservoir to the outlet of the device for delivery of the medication to the desired location in an body, usually through a catheter. These devices are used to provide patients with a constant and long term dosage or infusion of a drug or other therapeutic agent. Over time, the drug or other sterile solution becomes depleted and it is necessary to refill the device with a new supply of drug. This is commonly done by providing the device with a fill port that is typically covered with a resilient resealable septum which is accessible by injecting a hypodermic needle through the skin and into the septum thereby providing access to refill the reservoir.

Implantable infusion devices may be categorized as either passive or active. Passive drug infusion devices rely upon a pressurized drug reservoir to deliver the drug. Thus, such devices tend to be both smaller as well as cheaper as compared to active devices. An example of such a device includes the Medtronic IsoMed. This device delivers the drug into the patient through the force provided by a pressurized reservoir applied across a flow control unit.

Active drug or programmable infusion devices feature a pump or a metering system to deliver the drug into the patient's system. An example of such a drug infusion pump currently available is the Medtronic SynchroMed programmable pump. Additionally, U.S. Pat. No. 4,692,147 (Duggan), assigned to Medtronic, Inc., Minneapolis, MN., discloses a body-implantable electronic drug administration device comprising a peristaltic (roller) pump for metering a measured amount of drug in response to an electronic pulse generated by control circuitry associated with the device. The applicant specifically incorporates U.S. Pat. No. 4,692,147 (Duggan) by reference.

Such devices include a drug reservoir, a fill port, a pump to pump out the drug from the reservoir, and a catheter port. A catheter, connected to the catheter port, transports the pumped out drug from the device to a patient's anatomy. Such devices also typically include a battery to power the pump as well as an electronic module to control the flow rate of the pump. The drug reservoir, fill port, pump, and catheter port are generally held in a housing, commonly called a chasis or bulkhead, which is the main structural component of the drug infusion pump. The bulkhead typically has a series of passages from the drug reservoir and through the pump that lead to the catheter port which is located on the side of the housing.

It is advantageous to provide an implantable drug infusion devices with a means for injecting medication or other therapeutic agents directly into the catheter. In such instances, a catheter access port may be provided in addition to the fill port. The catheter access port will generally have a resilient resealable septum that is accessible percutaneously by hypodermic needle. This septum provides direct access to the catheter bypassing the primary fluid passageway and allows the medication to be administered directly into the body at the site of the catheter. Alternatively, the catheter may be used to remove or extract fluids, such as blood, from a patient.

Prior art implantable drug delivery devices are typically cylindrical in shape. These devices typically include a top shield, a bottom shield, and a bulkhead. The bulkhead is typically disk-shaped. Attached to the bulkhead are various subassemblies. Catheter access ports, filters, over pressure mechanisms, fill ports, and pump mechanisms are examples of such sub-assemblies. A disk-shaped bottom shield is connected to the bulkhead and forms a space for a drug reservoir. A bellows may be located in this space. After the pump components, battery and electrical components, and subassemblies are connected to or placed within the bulkhead, the top and bottom shields are attached to the bulkhead. The top shield, bottom shield, and bulkhead combine to form a hermetic enclosure.

While the prior art devices operate satisfactorily, they are relatively expensive to manufacture and to assemble. Certain disadvantages associated with the design of prior art devices contributes to the expensive of manufacturing and difficult assembly of prior art devices. In particular, bulkheads for implantable drug infusion pumps do not fully integrate all subassemblies into the bulkhead. Rather, certain subassemblies are separated from the bulkhead and attached to the bulkhead during assembly. For example, in the SynchroMed and other prior art drug infusion devices, the catheter access port is a separate component that is attached to the outside of the bulkhead portion of prior art drug infusion devices. Attaching the catheter access port requires additional and often expensive and complicated manufacturing steps. Typically, a catheter access port is either welded or attached with a silicone medical adhesive to the outside of the bulkhead. Attaching other subassemblies to the bulkhead results in similar added expense and manufacturing complexities.

SUMMARY OF THE INVENTION

The present invention provides an implantable drug infusion device which features a bulkhead having integrated subsystems. By integrating subassemblies, into the bulkhead, manufacturing efficiencies are created. For example, integrating the catheter access port into the bulkhead eliminates the manufacturing step of welding the catheter access port to the bulkhead from the assembly of implantable drug infusion pumps. Thus, the present invention provides significant cost-savings opportunities and creates fewer production problems.

The manufacturing benefits achieved by the integration of subassemblies into the bulkhead include: a reduction in the number of components to assemble, an elimination the number of manufacturing steps, and a reduction in manufacturing costs. Another advantage of the present invention, greater control and accuracy in the connections between the various subassemblies, results from integrating the fluid system into the bulkhead. Thus, the present invention eliminates the expense and assembly difficulties associated with prior art drug infusion devices while improving the accuracy of the drug dosage delivered by the pump.

In a preferred embodiment, the catheter access port is integrated into the bulkhead. This eliminates the need to manufacture this as a separate component and eliminates the manufacturing step of attaching this component to the completed assembly. In addition to integrating the catheter access port features into the bulkhead, the preferred embodiment of the bulkhead of the novel drug infusion device has key features of other subassemblies built into it. For example, portions of the pump, pump race, fill-port, over pressure mechanism, filter, and fluid pathway features of other subassemblies may be advantageously integrated into the bulkhead.

In another preferred embodiment of the present invention, the entire fluid pathway is integrated into the bulkhead. This can be readily accomplished by simple drilling and/or surface milling operations so that precise manufacturing and assembly may be achieved and greater control and accuracy of the connections between subassemblies achieved. Greater control of these connections allows for a more precise metering of medication through the device.

BRIEF DESCRIPTION OF THE DRAWINGS

The accompanying drawings, which are incorporated into and form a part of this specification, illustrate several embodiments of the present invention and, together with the description, serve to explain the principles of the invention. The drawings are only for the purpose of illustrating a preferred embodiment of the invention and are not to be construed as limiting the invention. The above mentioned and other advantages and features of the invention will become apparent upon reading the following detailed description and referring to the accompanying drawings in which in which like numbers refer to like parts throughout and in which.

DESCRIPTION OF THE PREFERRED EMBODIMENTS

Figure 1:
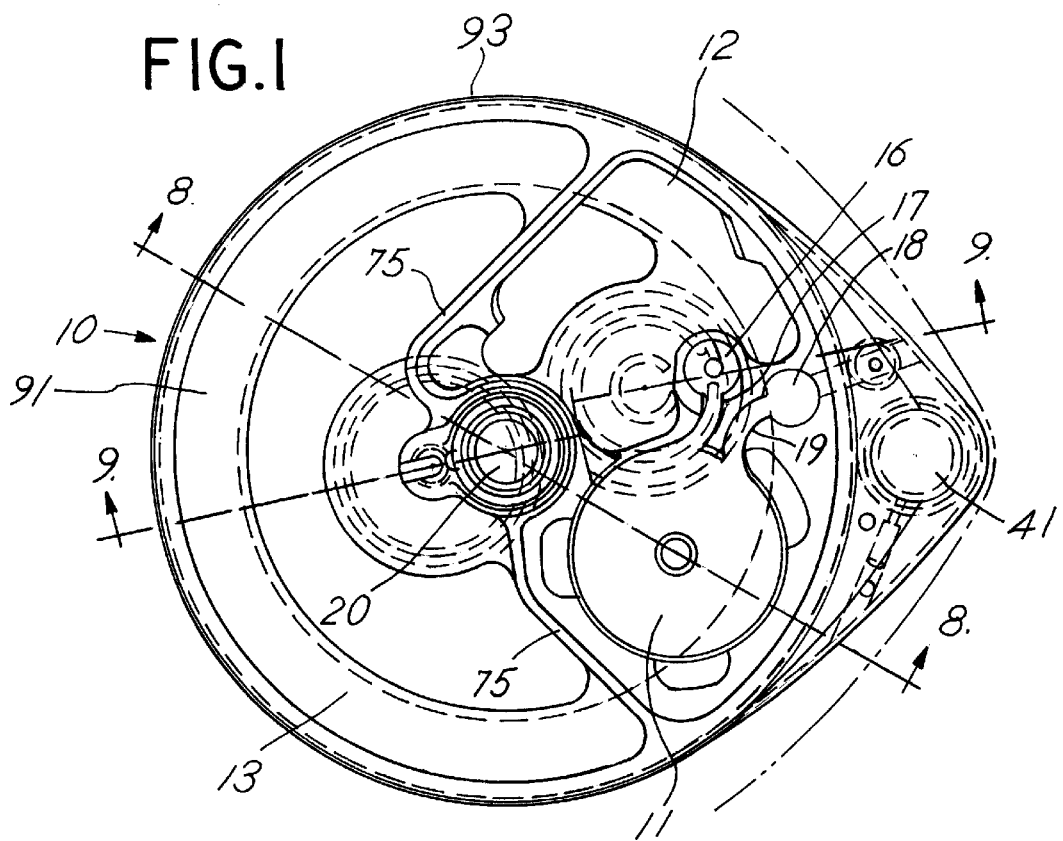
FIG. 1 is a top view of a preferred form of the bulkhead with the structures of the bottom surface of the bulkhead shown in shadow.
Figure 2:
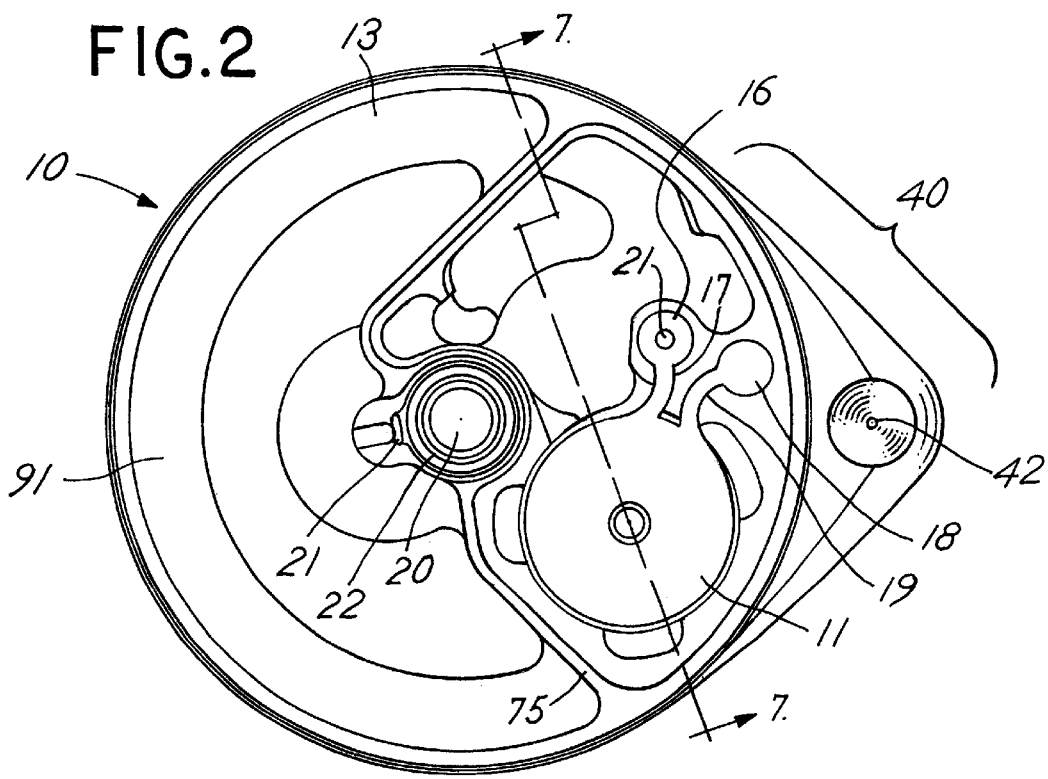
FIG. 2 is a top plan view of the bulkhead shown in FIG. 1.
Figure 3:
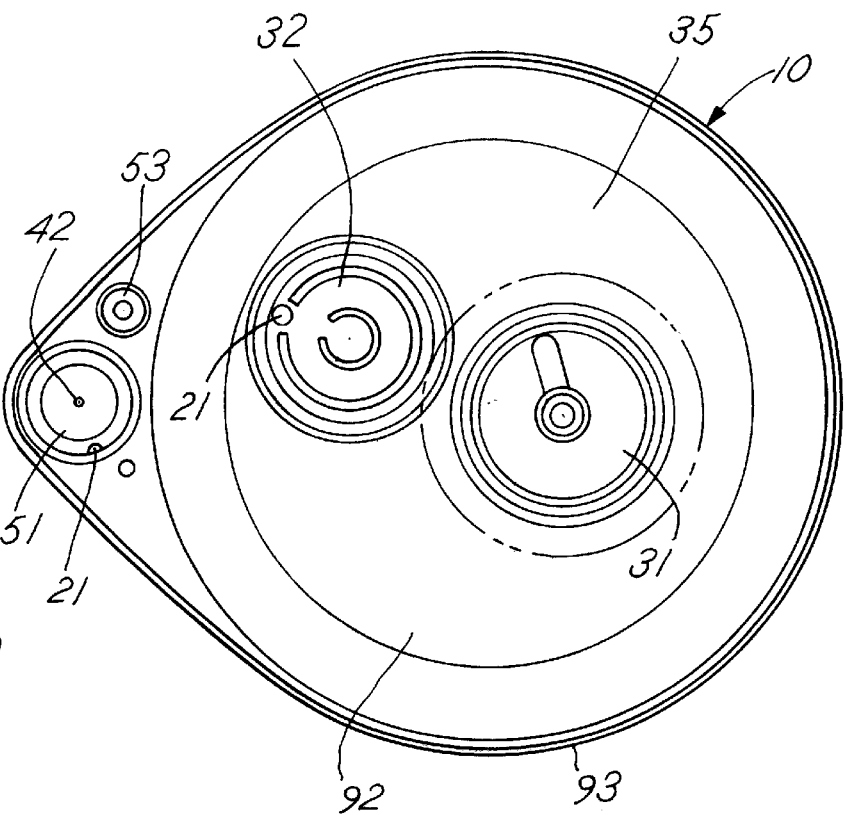
FIG. 3 is a bottom plan view of the bulkhead shown in FIG. 1.

FIG. 1 generally depicts the bulkhead 10 of the present implantable drug infusion device 5. Referring to FIGS. 1, 2, and 3, the bulkhead has an upper surface 91, lower surface 92, and a periphery 93. The upper surface 91 of the bulkhead 10 contains a number of built-in chambers, cavities, and pathways sized and configured to house various subsystems of the implantable drug infusion device. Embodiments of the bulkhead of the invention 10 may have all or portions of one or more of the following subassemblies: pump, motor and gear train, fill port, filter, over pressure mechanism, catheter access port, fluid system, and electronics, built-in to the bulkhead 10. Integrating these subassemblies into the bulkhead provides significant cost saving opportunities and eliminates manufacturing problems.

The bulkhead may also be referred to as a chassis by those of skill in the art. The bulkhead 10 is preferably disk shaped and machined from a single piece of bio-compatible material, such as stainless steel, plastics, titanium or other material suitable for implantation into the human body. Other geometries are contemplated for the bulkhead 10 and for the implantable drug infusion device 5. Depending on the desired subassemblies selected for a particular implantable drug infusion device 5, the bulkhead 10 may be formed from more than a single piece of material without deviating from the true scope of the invention.

Referring to FIG. 2, the upper surface of the preferred embodiment of the bulkhead 10 has an first upper chamber 11 sized and configured to house a pump assembly. Suitable pumps are known in the arts and include peristaltic pumps, solenoid pumps, diaphragm pumps, piston pumps, piezoelectric pumps and other like known pumps. The specific size and configuration of the first upper chamber, or pump assembly chamber, 11 will depend on the size and shape of the specific pump assembly selected for use in the implantable drug delivery device.

A second upper chamber 12 sized and configured to house a motor and gear train assembly for operating the pump assembly may be positioned adjacent the first upper chamber 11. In a preferred embodiment shown in FIG. 2, the first upper chamber 11 and second upper chamber 12 are configured in an essentially co-planar geometry. Depending on orientation and type of pump selected for use in the implantable medical device, a second upper chamber 12 may not be present. For example, the pump and motor assembly may be located on top of each other, as shown in U.S. Pat. No. 4,692,1.47 (Duggan), which would obviate the need for a motor and gear train chamber.

The upper surface of the bulkhead 10 may also include a third upper chamber 13 sized and configured to house a battery and electronic circuitry. The battery and electronic circuitry are used to operate the implantable drug infusion device and to control the dosage rate of the medication into the body. While it is preferred that one chamber house both the battery and electronic circuitry, bulkheads with other configurations for these components is contemplated as being within the scope of the present invention. The size and configuration of the electronics and battery chamber will be dictated y the particular electronics and battery designated for use in the implantable drug infusion device.

In a preferred embodiment shown in FIG. 2, the first upper chamber 11, second upper chamber 12, and third upper chamber 13, are preferably located within a circular region 95 of the upper surface 91 of the bulkhead 10. In a preferred embodiment, the center of the circular region 95 is defined by the center port of the fill port cavity 20. While FIG. 2 shows a bulkhead 10 having a circular region, one of skill in the art would consider other geometries, such as rectangular, oval, elliptical, triangular, and other like geometries, within the scope of the present invention. Walls 75 separate the first upper chamber 11 second upper chamber 12, and third upper chamber 13.

The first upper chamber 11 has a generally circular portion defining a pump race. The pump race is designed and sized to accept a pump tube. A portion of the tube is placed in the pump race in close proximity to the wall 75 of the first upper chamber 11 so that the means for compressing the tube may force the tube against the wall thereby forcing medication to move through the tube. The inlet to the pump tube is placed in a pump inlet cavity 16. The pump inlet cavity 16 is connected to the pump race by a pump inlet race ramp 17. The pump tube outlet is placed in the pump outlet cavity 18. The pump tube outlet cavity 18 is connected to the pump race by a pump outlet race ramp 19. In a preferred embodiment, both the pump inlet race ramp 17 and the pump outlet race ramp 19 have an arcuate geometry. The pump inlet cavity 16 has an orifice 21 there by creating a fluid pathway between the pump inlet cavity and a second lower chamber 32 which is located on the lower surface of the bulkhead 10. The pump outlet cavity 18 preferably has an orifice 21 on the side of the pump outlet cavity thereby creating a fluid pathway between the pump outlet cavity 18 and a catheter port 60 located on the periphery of the bulkhead 10.

Additionally the pump inlet cavity 16, pump inlet race ramp 17, pump outlet cavity 18, and pump outlet race ramp 19, either above or in combination, may be rendered unnecessary depending on the choice of pump assembly. In such an embodiment, the first upper chamber 11 would be provided with an inlet means for creating a fluid pathway between the drug reservoir (either directly or indirectly) and the first upper chamber 11 and an outlet means for creating a fluid pathway (either directly or indirectly) between the first upper chamber 11 and a catheter port 60. Suitable inlet and outlet means may include passageways, conduits, orifices, bores, channels, walls, tubes or other known structure suitable for directing the flow of a fluid. Accordingly, the drawings are only illustrative of the preferred embodiments of the invention and the applicants contemplate bulkheads sized and configured differently than as shown as being within the scope of their invention.

Figure 4:
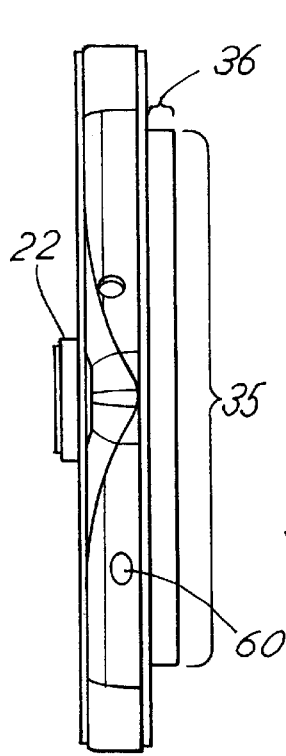
FIG. 4 is a side profile of the bulkhead shown in FIG. 1.
Figure 5:
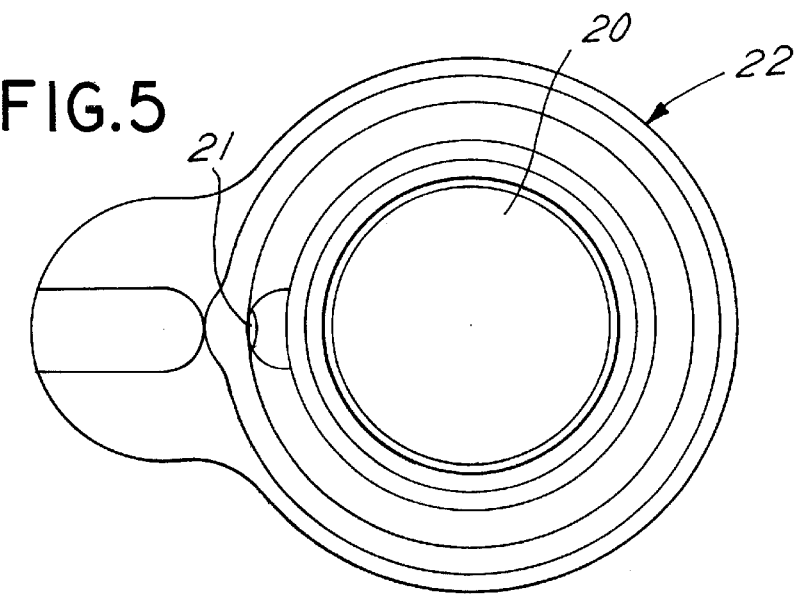
FIG. 5 is an exploded partial plan view of the top surface of the bulkhead shown in FIG. 1 illustrating the fill-port cavity.
Figure 6:
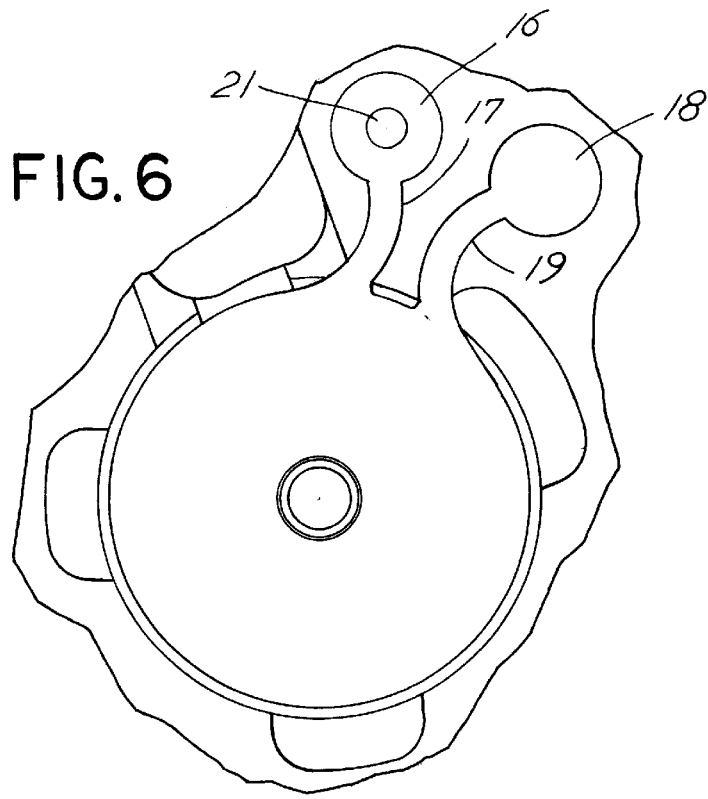
FIG. 6 is an exploded partial view of the top surface of the bulkhead shown in FIG. 1 illustrating the pump chamber.
Figure 7:
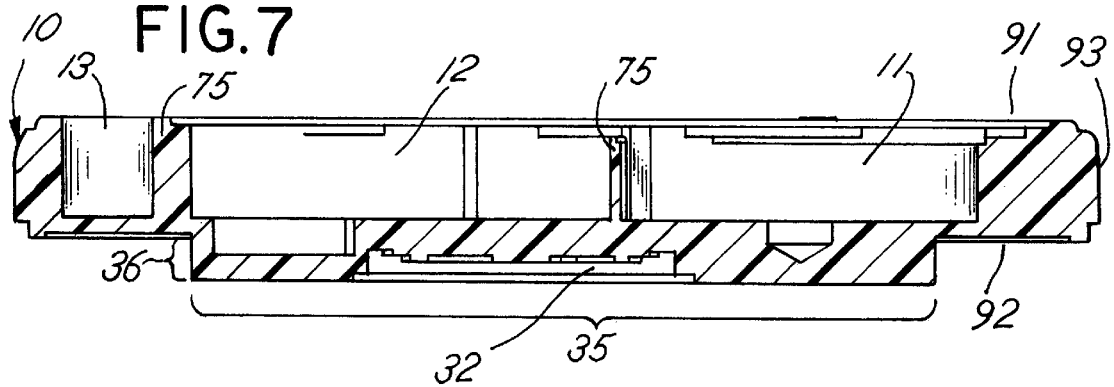
FIG. 7 is a cross sectional view of the bulkhead shown in FIG. 2 along the line 7—7.
Figure 8:
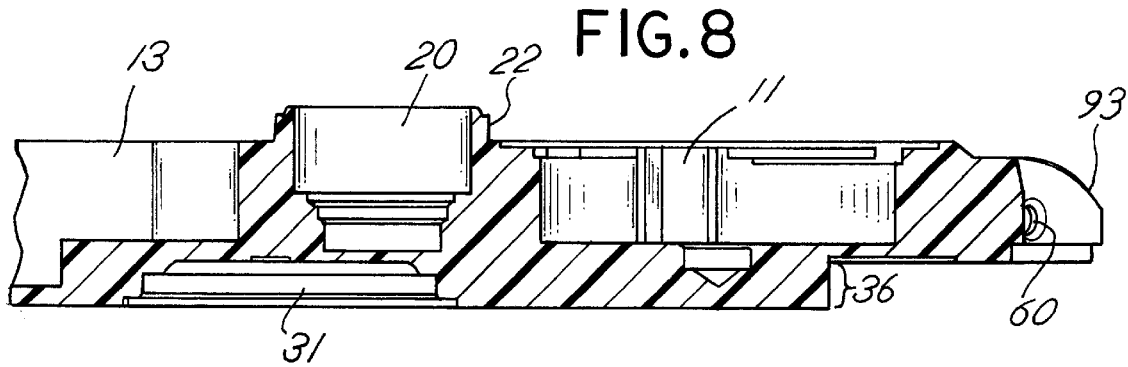
FIG. 8 is a cross sectional illustration of the bulkhead shown in FIG. 1 along the line 8—8.
Figure 9:
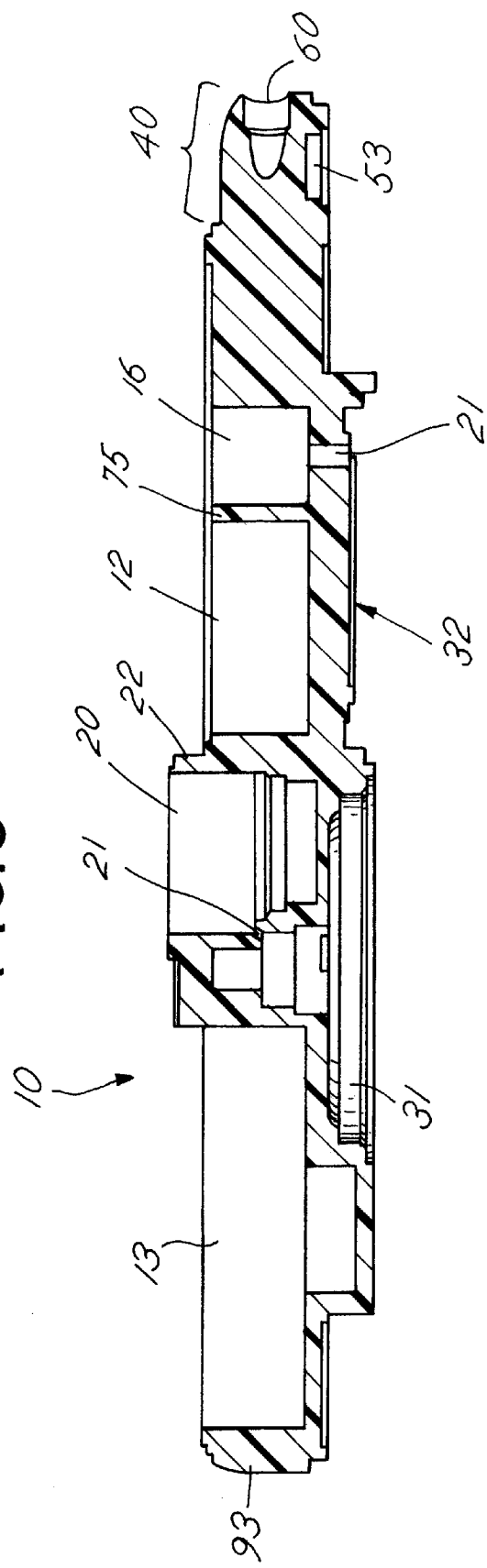
FIG. 9 is a cross sectional view of the bulkhead shown in FIG. 1 along the line 9—9.

Referring to FIGS. 1, 3, 4 and 5, the bulkhead 10 has an integral fill port cavity 20 on the upper surface of the bulkhead 10. The fill port cavity 20 is preferably sized and configured to house a septum and components to retain the septum. As shown in FIGS. 2 and 5, the fill port cavity 20 preferably has a generally circular geometry and is located in the central portion of the bulkhead 10. The fill port cavity has a cylindrical wall 22. As best shown in FIG. 4, an upper portion of the wall 22 of the fill port cavity 20 rises above the plane in which the first upper chamber 11, second upper chamber 12, and third upper chamber 13 are positioned. As shown in FIGS. 5 and 9, the inner portion of the cylindrical wall 22 of the fill port cavity 20 includes an orifice 21. The orifice 21 creates a fluid pathway between the fill port cavity 20 and a first lower chamber 31 located on the lower surface of the bulkhead 10.

Although the fill port cavity 20 preferably has a circular geometry and is centrally located, other geometries and locations for the fill port cavity 20 are contemplated by the applicants and considered within the scope of the invention. For example, the fill port cavity could be located near the periphery of the bulkhead and have a rectangular geometry without deviating from the true scope of the applicants' invention.

Figure 13:
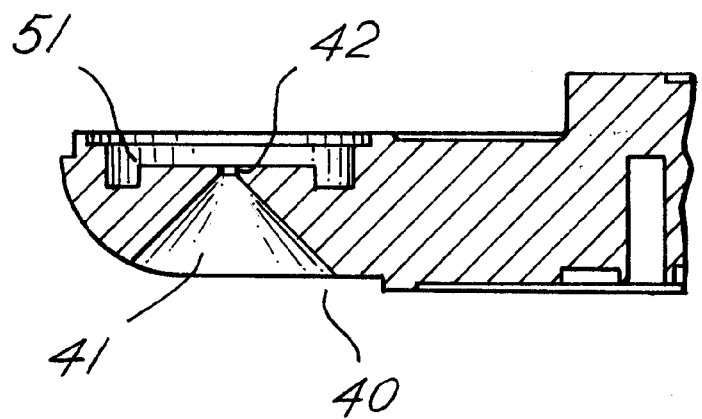
FIG. 13 is an exploded partial cross sectional the bulkhead shown in FIG. 12 illustrating the catheter access port.

The bulkhead 10 has a preferably triangular shaped portion having one arcuate edge adjacent the circular region 95 of the upper surface 91. This triangular shaped region, labeled generally as 40, defines the catheter access port 40. The catheter access port 40 includes a secondary fluid pathway that allows medical personnel to inject medications or sterile solutions directly into a catheter, bypassing the primary fluid pathway of the drug infusion device that is primarily defined by the bulkhead 10. Additionally, medical personnel may use the secondary pathway to extract fluids, such as blood, from a patient. Referring to FIG. 2, the catheter access port 40 has an upper catheter access port cavity 41 on the upper surface of the bulkhead 10 sized and configured to hold a septum and components for the septum. Structure of the septum and retaining components are known to one of skill in the art. In a preferred embodiment, FIG. 13 shows the upper catheter access port cavity 41 having a conical geometry with the cylinder tapering to a point in the direction of the lower surface 92 of the bulkhead 10. As shown in FIGS. 3 and 13, The upper catheter access port cavity 41 has an axial bore 42 connecting the upper catheter access port cavity 41 with a lower catheter access port cavity 51 located on the lower surface 92 of the bulkhead 10.

FIG. 3 is a plan view of the lower surface 92 of the bulkhead 10. The lower surface 92 of the bulkhead 10 defines a datum plane. As shown in FIG. 4, the bulkhead 10 may have a region 35 having a height 36 descending from the lower surface 92. Preferably, the region 35 is generally circular in shape to correspond to the generally circular region 95 of the upper surface 91 of the bulkhead 10.

The lower surface 92 of the bulkhead 10 may include a first lower chamber 31 and a second lower chamber 32. Preferably, the first lower chamber a 31 and second lower chamber 32 are positioned within the region 35. The first lower chamber 31 is sized and configured to house an over pressure mechanism. During the filling or refilling of the drug reservoir, an over pressurization of the reservoir can occur depending upon the filling pressure. Thus, an over pressure mechanism prevents the drug infusion device from becoming over pressured when being filled with medication by medical personnel. Suitable over pressure mechanisms for placement in the over pressure mechanism chamber 31 are known to one of skill in the art, one example being U.S. Pat. No. 5,725,017 (Elsberry), assigned to Medtronic, Inc., Minneapolis, MN. The first lower chamber 31 communicates with the fill port cavity 20 via orifice 21.

The second lower chamber 32 is sized and configured to house a filter. The filter (not shown) operates to prevent bacteria and other foreign matter from passing into the pump assembly and on to the human body. As previously mentioned, the second lower chamber 32 is connected to the pump inlet cavity 16 by way of a orifice 21, or other like passageway such as a bore, conduit, that is machined, drilled, or milled into the chasis 10. Suitable filters for placement in the filter cavity 32 are known to one of skill in the art.

Referring still to FIG. 3, the lower catheter access port cavity 51 is preferably positioned outside the region 35. In one embodiment of the invention, an anti-flow block valve cavity 53 is located adjacent the lower catheter access port cavity 51. Both the lower catheter access port cavity 51 and the anti-flow back valve cavity 53 are preferably circular in configuration. An orifice 21 or other like passageway connects the lower catheter access port cavity 51 to the anti-flow back valve cavity 53 thereby creating a passage through which a fluid may travel. The anti-flow block valve prevents medication inserted into the catheter access port from flowing back towards the central interior region of the chasis 10 in the direction of the pump tube outlet cavity. A second orifice 21 connects the lower catheter port cavity 51 to the catheter port 60. The catheter port 60 is sized and configured to accept a catheter. Alternatively, the catheter port 60 is sized and configured to accept a catheter fitting 95, shown in FIG. 11, to which a catheter may then be attached.

Figure 11:
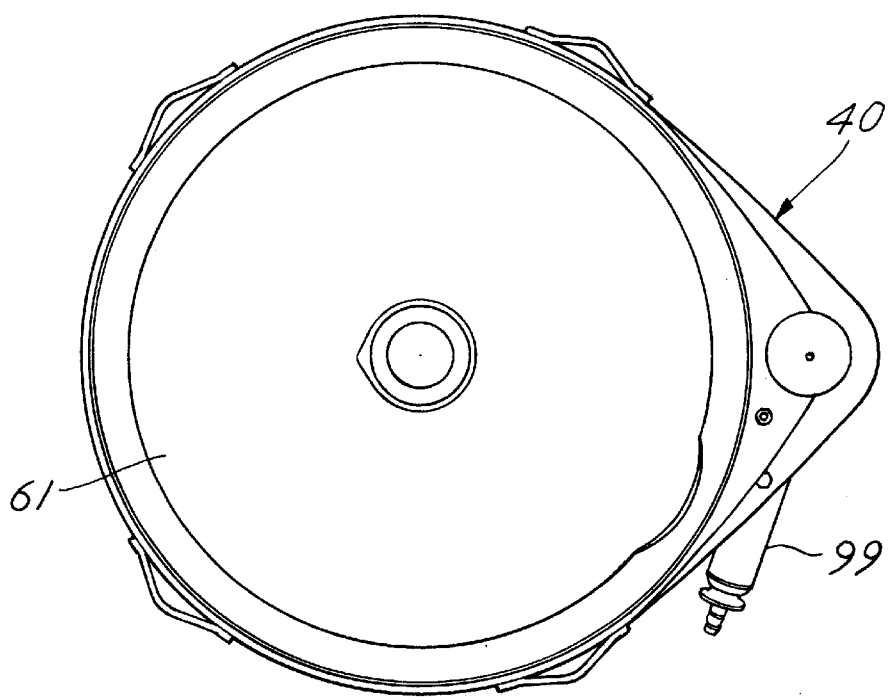
FIG. 11 is a plan view of the top surface of the assembled medical device.
Figure 10:
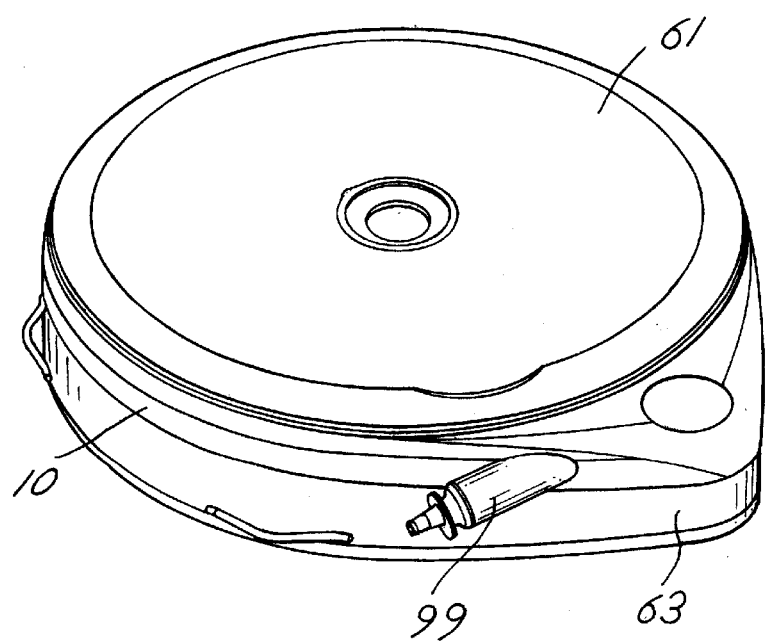
FIG. 10 is a perspective view of the top assembled medical device according to the present invention.
Figure 12:
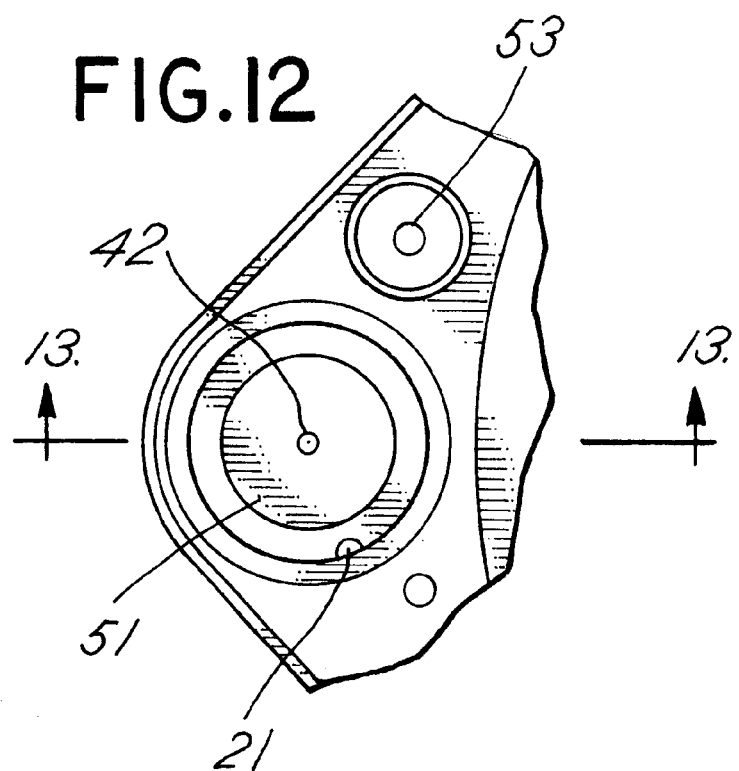
FIG. 12 is an exploded partial view of the bottom surface of the bulkhead shown in FIG. 1, illustrating the catheter access port.

FIGS. 11 and 12 show an assembled implantable drug infusion device 5 including the bulkhead 10 of the present invention. In this preferred embodiment, a top shield 61 and a bottom shield 63 attached to said bulkhead 10. Shields are also referred to as cans by those of skill in the art. The lower shield or can 63 has a top surface, and a side rising vertically from said top surface. The side of the lower shield or can 63 has a height greater than the height 36 of the region 35. Preferably, the lower shield 63 is sized and configured to enclose the region 35 thereby defining a space between the upper surface of the lower shield 63 and the lower surface 92 of the bulkhead 10 which defines a reservoir suitable for holding medication or other sterile solutions. Typically, a bellows (not shown) is placed within this space. The bulkhead 10 defines a primary fluid pathway from the reservoir to the catheter port 60 located on the periphery of the bulkhead 10. The catheter access port 40 defines a secondary fluid pathway whereby drugs maybe introduced into the catheter, bypassing the primary fluid pathway. In this embodiment, the drug reservoir communicates with the first lower chamber 31 and the second lower chamber 32. Preferably, the lower shield 63 is hermetically welded to the bulkhead 10. Other known means of joining the bulkhead to the lower cover 63 may also be used. Such means include for example the use of silicone medical adhesive, glue, epoxy, threaded joints, or other like connections. A suitable welding means such as the one disclosed in the U.S. Pat. No. 5,993,414 to Haller, assigned to Medtronic, Inc., Minneapolis, MN., may also be used. Preferably the lower shield 63 has a geometry corresponding to that of the bulkhead 10, as shown best shown in FIG. 11.

The upper shield 61 is sized and configured to enclose the circular region 95 located on the upper surface of the bulkhead 10. The upper shield 61 preferably has a centrally located hole 66 therethrough. The bore corresponds in dimension and configuration so that the upper shield 61 will snugly fit over the fill port cavity. The overall height of the assembled bulkhead 10, upper shield 61, and lower shield 63, preferably has a low profile.

The applicants also contemplates a new method of manufacturing a implantable drug infusion device which reduces the number of components for assembly, reduces the number of manufacturing steps, and provides significant cost-savings over current methods of manufacture. Additionally, the method of manufacturing of the present invention results in a simplifies production and reduced the number of production problems.

To begin manufacturing the bulkhead for use in the present invention, a bio-compatible metal, preferably titanium, or other material suitably non-reactive in the human body is provided. The material is machined into a disk like structure, having a top surface, a bottom surface, and a periphery or alternatively could be formed using casting, forging, injection molding, either alone or in combination with machining. Preferably, the disk like structure has a central, circular region and a triangular shaped region having an arc shaped edge lying adjacent the circular region. The disk like structure is machined into a bulkhead for use in an implantable drug infusion device, said bulkhead divided into a plurality of integral cavities separated by walls. The bulkhead may have one or more of the following cavities sized and configured to house: a fill port, a pump assembly, an electronics and batteries, a motor, and an access catheter port. The bulkhead is additionally provided with one or more catheter ports along the periphery of the bulkhead. In a preferred method of manufacture, the bulkhead is provided with the motor cavity and pump cavity. In one embodiment, those cavities are positioned in an essentially coplanar geometry. Orifices, bores, or other passages are formed by drilling and/or surface milling operations so that selected cavities are connected to create a fluid pathway allowing medication to be injected into the implantable medical device, flow through said device, and flow out the catheter port into a catheter for localized treatment of an organ in an anatomy.

The preferred embodiments of the invention are now described as to enable a person of ordinary skill in the art to make and use the same. Variations of the preferred embodiment are possible without being outside the scope of the present invention. Therefore, to particularly point out and distinctly claim the subject matter of the invention, the following claims conclude the specification.

What is claimed is:

1. An implantable medical device for the infusion of a drug through a catheter into an anatomy, said medical device comprising:
   a drug reservoir;
   a bulkhead, said bulkhead including:
      (a) an integral fill port cavity,
      (b) an integral over pressure mechanism cavity, said over pressure mechanism cavity communicating with said fill port cavity,
      (c) an integral filter cavity, said filter cavity communicating with said drug reservoir,
      (d) an integral pump chamber, said pump chamber communicating with said drug reservoir,
      (e) an integral catheter port, said catheter port communicating with said pump chamber, whereby said fill port, said over pressure mechanism cavity, said filter cavity, said drug reservoir, said pump chamber, and said catheter port defining a first fluid pathway allowing a drug to enter said medical device, pass through said medical device, and exit said device through the catheter port into a catheter; and
      (f) an integral catheter access port, said catheter access port defining a second fluid pathway allowing a drug to enter said catheter, bypassing said first fluid pathway.

2. An implantable medical device for the infusion of drugs having an integrated bulkhead comprising:
   a bulkhead including a first chamber, a second chamber, and a catheter access port, said first and second chambers being essentially co-planar, said first chamber configured and sized to house a peristaltic pump assembly; said second chamber configured and sized to house a motor assembly.

3. An implantable drug infusion medical device, said device comprising:
   a bulkhead including a pump assembly chamber, a motor assembly chamber, and an integral catheter side access port, said pump assembly chamber adjacent said motor assembly chamber, said bulkhead formed from a single piece of bio-compatible material.

4. An implantable medical device for the infusion of drugs contained in a fluid comprising:
   an upper shield;
   a bulkhead, said bulkhead having an upper surface, a lower surface, and an outer periphery;

said lower surface of said bulkhead defining a datum plane, said bulkhead having a plateaued region descending from said datum plane, said region having a height, said region including a first lower chamber and a second lower chamber, said first lower chamber sized and configured to house an over pressure mechanism, said second lower chamber sized and configured to house a filter;

a lower shield, said lower shield having an upper surface, a lower surface, and a side rising vertically from said upper surface, said side having a height greater than the height of said region, said lower shield sized and configured to enclose said region thereby defining a space between said upper surface of said lower shield and said lower surface of said bulkhead said upper surface of said bulkhead including a centrally located fill port cavity, said fill port cavity housing configured and sized to house a fill port assembly, said fill port cavity having a wall; said wall having an orifice thereby creating a fluid pathway between said fill port cavity and said first lower chamber;

said upper surface of said bulkhead including a pump inlet cavity and a pump race inlet ramp, said pump inlet cavity having an orifice thereby creating a fluid pathway between said pump inlet cavity and said second lower chamber, said pump inlet cavity communicating with said pump race inlet ramp;

said upper surface of said bulkhead including a first upper chamber, said first upper chamber sized and configured to house a peristaltic pump assembly, said first chamber defining a circular pump race, said first chamber communicating with said pump race inlet ramp;

said upper surface of said bulkhead including a pump race outlet ramp and pump outlet cavity, said pump outlet cavity having an orifice, said pump race outlet ramp communicating with said first upper chamber, said pump race outlet ramp communicating with said pump outlet cavity;

said periphery of said bulkhead having a catheter port, said catheter port conmunuicating with said pump outlet cavity;

said upper surface of said bulkhead including an upper catheter access port cavity, said said lower surface of said bulkhead including a lower catheter access port cavity, said lower catheter access ports positioned outside said region, said upper and lower catheter access cavities connected by an axial bore thereby creating a fluid pathway between said upper and lower catheter access cavities;

said upper surface of said bulkhead including a second upper chamber, and a third upper chamber, said second upper chamber configured and sized to house a motor assembly, said third upper chamber configured and sized to house electronics for operating said medical device, said first, second, and third upper chambers being essentially co-planar, said first, second, and third chambers separated by walls.

5. A method of manufacturing a medical device for the infusion of drugs into an anatomy, said method comprising:

providing a singular block of material; and forming said material into a bulkhead, said bulkhead having a plurality of integral cavities, said cavities including an electronics cavity, a motor cavity, a pump cavity, said electronics, motor, and pump cavities being essentially co-planar.

* * * * *